CARNATION PLANT
Filed Feb. 11, 1972 2 Sheets-Sheet 1
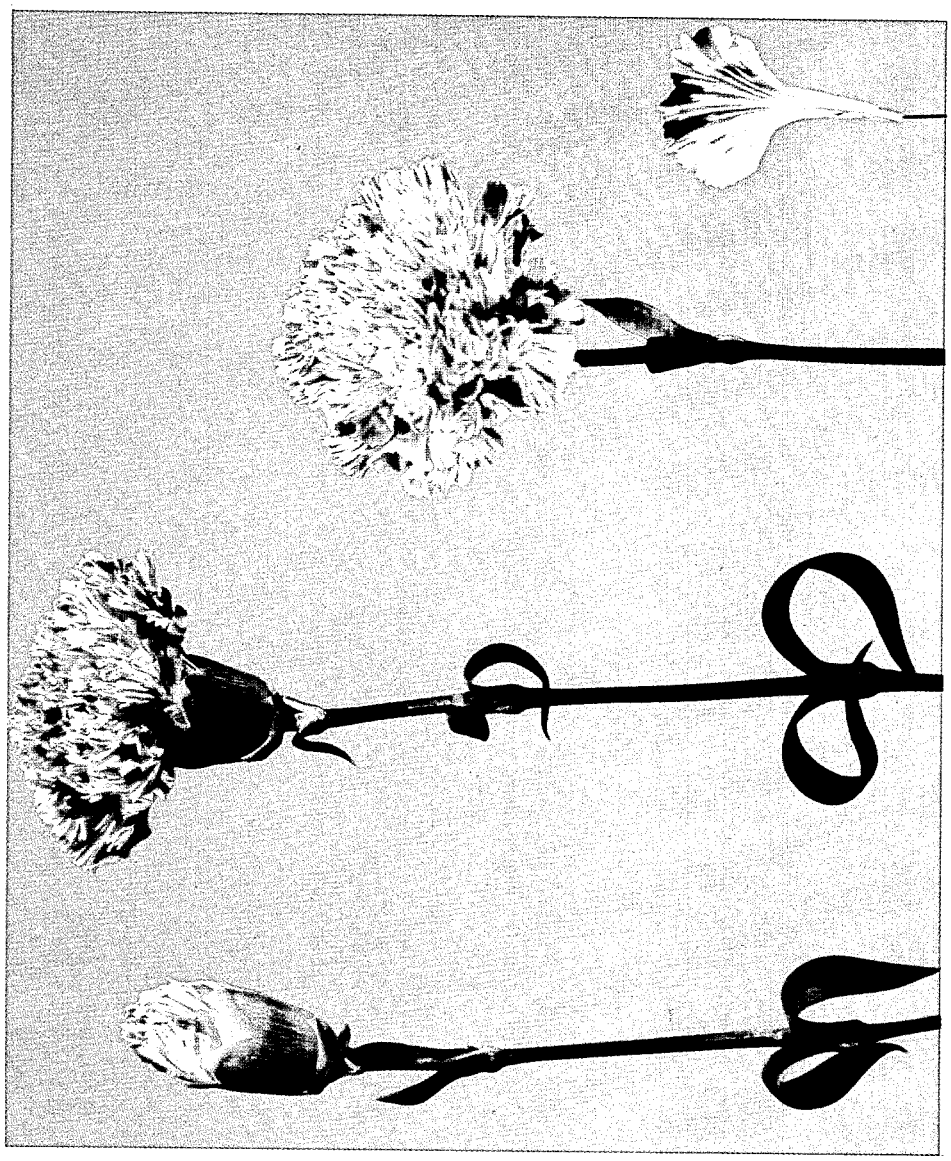

CARNATION PLANT
Filed Feb. 11, 1972 2 Sheets-Sheet 2
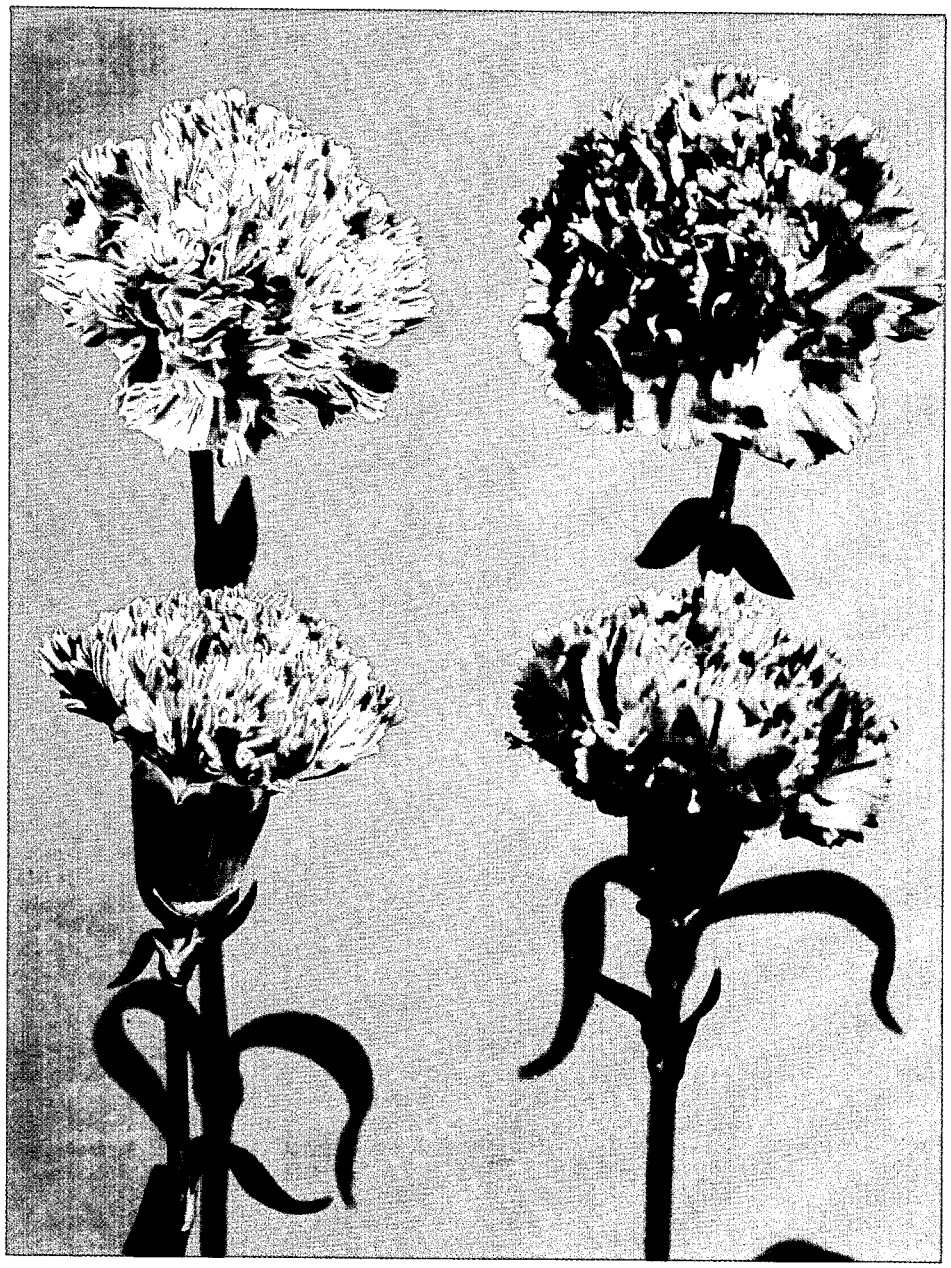

United States Patent Office

Plant Pat. 3,554
Patented May 21, 1974

3,554
CARNATION PLANT

Peter F. Mazzanti, South San Francisco, and Thomas G. Harcharik, Salinas, Calif.; said Harcharik assignor to said Mazzanti

Filed Feb. 11, 1972, Ser. No. 225,684
Int. Cl. A01h *5/00*
U.S. Cl. Plt.—70 1 Claim

The present invention comprises a new and distinct cultivar of carnation plant which is a sport of the cultivar known in the United States as Tangerine Sim. The latter was registered with the American Carnation Society, Philadelphia, Pennsylvania, in 1958, by the E. W. McLellan Company, P.O. Box 111, 2450 Depot Road, Mt. Eden, California 94557. Tangerine Sim is disclosed and illustrated in U.S. Plant Pat. No. 1,734, issued July 29, 1958.

The new cultivar is similar in many respects to Tangerine Sim, having the same characteristics of:

1. Growth habit and vigor.
2. Stem length and stem strength.
3. Flower form.
4. Keeping and shipping quality.
5. Annual production per square foot.
6. Crop response on first cut and return crops.
7. Foliage size, shape and color.

The new cultivar is distinguished from Tangerine Sim by the following characteristics when grown under comparable conditions:

1. A bi-colored or variegated color of broad orange stripes on a white background.

2. A flower approximately ¼"–½" smaller in diameter.

3. A slightly lower petal count. (Approximately 10 petals less.)

The new cultivar was discovered as a flowering plant in South San Francisco, California, and when asexually reproduced by cuttings at Salinas, California, has been found to retain its distinctive characteristics through successive propagations.

The following detailed description is based on observations made of the new cultivar in a greenhouse in Salinas, California. The response time, blooming period, total vigor, and color may vary significantly with varying environmental conditions such as temperature, day length and light intensity.

The accompanying photographic drawings show the unique characteristics of the new cultivar, the color being as nearly true as possible with color illustrations of this type. Sheet one illustrates the new cultivar itself, from budding through a fully open condition. Sheet two comprises a comparison photograph, with the new cultivar appearing on the left and the parent cultivar Tangerine Sim on the right. It should be noted that when viewed under fluorescent lighting, the phoographs tend to show the flower color slightly darker than the actual color when viewed in natural light conditions, or under incandescent lighting.

In the description which follows, color references are made to the Munsell Color Book, 1963 edition, and comparisons are made with the cultivar Tangerine Sim. Where only a single value or description appears for the new cultivar, the same value or description applies to the parent cultivar as well.

Botanical classification: *Dianthus caryophyllus*

| | Orange chip | Tangerine Sim |
|---|---|---|
| Bloom: | | |
| Type | Disbud | |
| Size (diameter in inches) | Approximately 2½"–3¼" | Approximately 3"–3½". |
| Petal edge | Serrated | |
| Petal count | Approximately 60 | Approximately 70. |
| Petal texture | Smooth | |
| Petal size: | | |
| Average length | 2⅛" | |
| Average width | 1⅜" | 1 ". |
| Bud shape | Ovoid | |
| Splitting tendency | Low | |
| Slab tendency | Slight | |
| Keeping quality | Approximately 10–12 days | Moderate. |
| Fragrance | Mild | |
| Color: | | |
| Center of flower | Pale ivory pink 5YR9/1 striped orange 8.75R5/12, to light orange 8.75R6/12. | Orange 8.75R5/12 to light orange 8.75R6/12. |
| Base of petals | Light yellow green, 2.5GY8/6 | Light yellow green, 2.5GY8/6. |
| Base color | Pale ivory pink, 5YR9/1 | Orange 8.75R5/12 to light orange 8.75R6/12. |
| Stripes | Pale ivory pink, 8.75R5/12 to 10R7/8 orange to light orange | No stripes. |
| Color stability | 3.5–4.5% reversion to Tangerine Sim | Uniform. |
| Seasonal variations | Stripes observed as light orange 10R7/8 during high temperature, high light intensity periods. | Light orange 10R7/8. |
| Reproductive organs: | | |
| Stamen, anthers | White N9/ | White N9/. |
| Pollen | Tan, 5YR 2 | Tan, 5Y9/2. |
| Stigma | 2–3 lobes white N9/ | 2–3 lobes, white N9/ streaked on reverse with orange 8.75R6/12. |
| Styles | White N9/ | |
| Length | 1⅜"–1½" | |
| Ovaries: | | |
| Tip | Tan 5Y6/8 | |
| Mid | Ivory 10Y9/1 | |
| Base | Yellow green 2.5GY6/8 | |
| Calyx: | | |
| Size | 1¼" | |
| Shape | Bell-shaped | |
| Number of sepals | 5 | |
| Stems: | | |
| Length | Approximately 18–22" | |
| Bending traits | One o'clock | |
| Plant: | | |
| Form | Erect and branching bush | |
| Growth | Vigorous, strong, sturdy and upright | |
| Height | Approximately 38", when grown as a 1 year, single pinch crop, at a spacing of 3 plants per square foot. | |
| Foliage: | | |
| Topside (color) | Dark green 7.5GY3/4 | |
| Underside (color) | do | |
| Mature (color) | do | |
| Length (mature leaf) | 6"–7" | |
| Shape | Acicular | |
| Texture | Glaucous | |
| Displacement | Opposite | |

We claim:

1. A new and distinct cultivar of carnation characterized particularly as to its uniqueness when compared to the parent cultivar Tangerine Sim by its variegated color of broad orange stripes on a white background, its approximately ¼"–½" smaller diameter flowers, and its slightly lower petal count.

No references cited.

ROBERT E. BAGWILL, Primary Examiner

UNITED STATES PATENT OFFICE

CERTIFICATE OF CORRECTION

Patent No. PP-3554 Dated May 21, 1974

Inventor(s) PETER F. MAZZANTI and THOMAS G. HARCHARIK

It is certified that error appears in the above-identified patent and that said Letters Patent are hereby corrected as shown below:

In the tabulated description below Columns 1 and 2:

Approximately line 3, opposite "Size", under the cultivar "Orange Chip", should read --approximately 2-3/4" - 3-1/4"--;

Approximately line 9, under "Petal size:", opposite "Average width", under the cultivar "Tangerine Sim", change "1" " to --1-3/4"--; and Approximately line 23, under "Reproductive organs:", opposite "Pollen", under the cultivar "Orange chip", the description should read --Tan, 5Y9/2--.

Signed and sealed this 5th day of November 1974.

(SEAL)
Attest:

McCOY M. GIBSON JR.
Attesting Officer

C. MARSHALL DANN
Commissioner of Patents